United States Patent
Petersen et al.

(10) Patent No.: US 9,939,350 B2
(45) Date of Patent: Apr. 10, 2018

(54) DEVICE FOR THE EXPOSURE OF SAMPLE BODIES IN A FLUID

(71) Applicant: Helmholtz-Zentrum Geesthacht Zentrum für Material—und Küstenforschung GmbH, Geesthacht (DE)

(72) Inventors: Jördis Petersen, Lauenburg (DE); Daniel Pröfrock, Amelinghausen (DE); Volker Langhans, Hollenbek (DE); Andreas Prange, Hamburg (DE)

(73) Assignee: Helmholtz-Zentrum Geesthacht Zentrum Für Material-und Küstenforschung GmbH, Geesthacht (DE)

( * ) Notice: Subject to any disclaimer, the term of this patent is extended or adjusted under 35 U.S.C. 154(b) by 295 days.

(21) Appl. No.: 14/737,641

(22) Filed: Jun. 12, 2015

(65) Prior Publication Data
US 2015/0362409 A1 Dec. 17, 2015

(30) Foreign Application Priority Data
Jun. 17, 2014 (EP) .................................... 14172809

(51) Int. Cl.
*G01N 1/40* (2006.01)
*G01N 1/10* (2006.01)
(Continued)

(52) U.S. Cl.
CPC .............. *G01N 1/10* (2013.01); *G01N 1/2035* (2013.01); *G01N 1/405* (2013.01); *G01N 1/38* (2013.01)

(58) Field of Classification Search
CPC ....................................................... G01N 1/405
See application file for complete search history.

(56) References Cited

U.S. PATENT DOCUMENTS 3,801,280 A * 4/1974 Shah ...................... G01N 13/00
  210/359
3,946,596 A * 3/1976 Shiuh ..................... G01N 15/08
  162/198

(Continued)

FOREIGN PATENT DOCUMENTS

| GB | 1566253 A | 4/1980 |
|---|---|---|
| WO | WO-93/08258 A1 | 4/1993 |
| WO | WO-2013/132630 A1 | 9/2013 |

*Primary Examiner* — Robert R Raevis
(74) *Attorney, Agent, or Firm* — Harness, Dickey & Pierce, P.L.C.

(57) ABSTRACT

A device for exposing sample bodies to a fluid. The sample bodies have an active surface section that defines a measuring plane. The device includes a container, a sample body holder, and an agitating element. The container, which extends along a longitudinal axis, has an inlet, an outlet, a closed side wall, which extends along the longitudinal axis, and first and second end faces that extend transverse to the longitudinal axis. The sample body holder extends transverse to the longitudinal axis and holds at least one sample body so that its measuring plane extends perpendicular to the longitudinal axis in a first sample plane its active surface section faces away from the first end face. The agitating element driven in a rotating manner in a plane perpendicular to the longitudinal axis and is arranged on the side facing away from the first end face of the first sample plane.

15 Claims, 5 Drawing Sheets

(51) Int. Cl.
*G01N 1/20* (2006.01)
*G01N 1/38* (2006.01)

(56) References Cited

U.S. PATENT DOCUMENTS

| | | | | |
|---|---|---|---|---|
| 4,699,013 A | * | 10/1987 | Kroner | B01D 29/05 210/383 |
| 5,502,998 A | * | 4/1996 | Miller | G01N 1/2273 73/1.06 |
| 6,296,764 B1 | | 10/2001 | Guirguis et al. | |
| 2003/0180954 A1 | * | 9/2003 | Riviere | G01N 13/00 436/5 |

* cited by examiner

DEVICE FOR THE EXPOSURE OF SAMPLE BODIES IN A FLUID

CROSS-REFERENCE TO RELATED APPLICATIONS

This application claims the benefit and priority of European Patent Application No. 14172809.7, filed Jun. 17, 2014, the entire disclosure of which is incorporated herein by reference as if fully set forth in detail herein.

FIELD

The present disclosure relates to a device for the exposure of sample bodies in a fluid.

BACKGROUND

This section provides background information related to the present disclosure which is not necessarily prior art.

The field of environmental analysis has long known about the technique of exposing so-called passive samplers over a long period of time in the water of a body of water, in order that certain organic and inorganic pollutant compounds relevant to the quality of the water in the body of water are accumulated in the passive samplers. Subsequently, the accumulated quantity of the compounds in question can be extracted, and a time-averaged concentration of the pollutants in solution can be determined, in order to thus arrive at a determination concerning the pollution of the body of water. Such passive samplers are known for example from GB 1 566 253 A. However, there are also other passive samplers, such as the so-called Chemcatcher Metal sampler or the DGT sampler for example, which are used for the accumulation of inorganic pollutants.

Such passive samplers are designed to comprise a collection phase having high affinity for the target analytes, and this collection phase is usually separated from the water phase by a membrane, which forms the active surface section. The other surfaces of the sampler do not allow the substances in question to pass through them.

In principle, for their exposure, these passive samplers may be placed directly into the body of water arranged in special cages or supports, allowing the water there to move around them. However, the problem with this is that when the sampler remains in the body of water for a sufficiently long period of time, vegetation or other deposits build up on the active surface section, which results in decreased diffusion of the substances in question into the inside of the sampler in the collection phase. When the total quantity of the substances in question accumulated in the sampler is subsequently determined in order to thus also arrive at a determination concerning the pollution of the body of water, the deposits and the vegetation cause the pollution to be underestimated.

Another problem with this type of arrangement of the passive samplers directly in the body of water is the lack of information about the flow conditions at the flat active surface section. Since it is precisely this streaming around the active surface section that determines the degree of diffusion of the substances in question into the inside of the passive sampler, this lack of clarity further reduces the precision of the determination concerning the pollution of the body of water.

It is therefore fundamentally desirable for the passive samplers to be arranged in such a way that, on the one hand, there are defined flow conditions in the active surface section zone, and on the other hand, that deposits and vegetation are prevented from building up on the active surface section.

Gunold et al., Calibration of the Chemcatcher passive sampler for monitoring selected polar and semi-polar pesticides and surface water, Environmental Pollution 155 (2008) 52-60, has already described an arrangement not for the actual concentration measurement in the body of water, but rather for calibration under laboratory conditions, in which arrangement passive samplers are arranged on a rotationally driven holder in an open container, through which water containing organic substances is fed at a pre-defined flow rate. However, this setup has the disadvantage that the flow conditions at the active surface section of the passive sampler are still not precisely defined.

SUMMARY

This section provides a general summary of the disclosure, and is not a comprehensive disclosure of its full scope or all of its features.

In one form, the present teachings provide a device for the exposure of sample bodies, in particular passive samplers, in a fluid such as water, which ensures that flow conditions in the active surface section zone of the sample bodies or passive samplers, respectively, remain constant over a long period of time. This may be achieved, for example with an agitating element driven in a rotating manner in a plane perpendicular to the longitudinal axis of a container, which agitating element is arranged on the side facing away from the first end face of the sample plane defined by the active surface section.

In the sample body holder there may be arranged during the measurement operation sample bodies designed as so-called passive samplers, which are designed such that there is accumulation therein of certain substances contained in the water as pollutants, wherein these substances are diffused into the inside of the sample body through an active surface section.

In addition, the agitating element can ensure that the zone over the active surface section or active surface sections is constantly moved, in order that the fluid also is constantly being moved over the active surface sections. Thus, the flow characteristics can be clearly defined and reproducible in precisely the relevant zone, in which the passive samplers interact with the fluid or the water in such a way that they are able to absorb substances contained therein.

Furthermore, when the sample body holder can accommodate several sample bodies, it can be designed such that the measuring planes of the sample body defined by the active surface sections extend in a common sample plane or lie in this common sample plane. This has the advantage that all sample bodies are installed under identical flow conditions. Finally, a constant speed of rotation of the agitating element during the measurement period can ensure that the flow characteristics in this zone remain constant over the entire measurement period during which the passive samplers are arranged in the container.

In a device constructed in accordance with the teachings of the present disclosure, the fluid or the water, respectively, can be pumped through pipes into the inside of the container containing the sample bodies and can be also removed therefrom. This means that the device can optionally be installed away from the actual measurement site and is capable of only being connected to the measurement site via pipes. This permits a very flexible application, and it is even possible to use the device on a ship, or the like. Because the container is sealed by the end face, it is also possible to pump pressurized fluid or water, respectively, through the container and thus allow flow rate variation over a greater range, by comparison with an open container.

The agitating element can rotate around the longitudinal axis, and the first sample body holder can be designed to support several sample bodies in such a way that their center points parallel to the first sample plane have a uniform distance to the longitudinal axis. Thus, the sample bodies can be arranged in a circle around the longitudinal axis, and when there is a pre-defined rotation speed of the agitating element, the flow rate at the location of the sample body can be easily calculated. Furthermore, this flow rate can be identical for all sample bodies, so that they, too, are exposed to identical conditions.

Optionally, a second sample body holder can be provided in the container. The second sample body can also extends transverse to the longitudinal axis and which can be designed to also support at least one sample body in such a way that its measuring plane extends perpendicular to the longitudinal axis in a second sample plane, and such that the active surface section is facing away from the second end face, wherein the agitating element is arranged between the first and the second sample body holders. If the second sample body holder is designed to accommodate several sample bodies or passive samplers, it, too, can be constructed in such a way that the measuring planes extend in a common second sample plane or lie in this common second sample plane, respectively.

The first and the second sample body holder can be arranged in such a way that the sample bodies or passive samplers, respectively, arranged therein have their active surface sections facing each other and are arranged opposite each other. Between these sample bodies, the agitating element can be then arranged, which constantly moves the fluid or the water, respectively, over the sample bodies arranged in both sample body holders. Such an arrangement makes it possible to simultaneously expose a greater number of sample bodies in the water under clearly defined conditions. In particular, the second sample holder can also be designed such that it can support several sample bodies in such a way that their center points parallel to the second sample plane have a uniform distance to the longitudinal axis. Thus, for the sample bodies in the second sample holder, too, the flow rate can be calculated, and this can be the same for all sample bodies held in the second sample holder.

The inlet can be provided in one of the first or the second end faces, while the outlet can be provided in the other of the first or the second end faces. In such a construction, the arrangement of the inlet and the outlet in opposite end faces ensures that the container in which the sample body or sample bodies in the passive sampler form are arranged has a constant flow through it in the axial direction, with no possibility of the formation therein of dead zones in which water pools and is not constantly exchanged.

The agitating element can be designed such that it is connected to a drive shaft, which extends parallel to the longitudinal axis through one of the first and the second end faces, wherein the agitating element additionally comprises blades extending radially outwards from the drive shaft. Such a construction permits simple actuation of the externally controllable agitating element, and it is not necessary to provide in the inside of the container a drive which is encapsulated in a complex manner.

These blades can be detachably held on the drive shaft. This can be advantageous because then access to the sample bodies accommodated in the sample body holder is facilitated when the blades are removed from the drive shaft.

The first end face can be detachably connected to the side wall, wherein the drive shaft extends through the second end face and the first sample body holder is detachably held on the side wall. In such a construction, to swap the sample bodies, the procedure may be to initially detach the first end face from the side wall and then take the first sample body holder arranged adjacent to the first end face out of the container. Then the sample bodies or passive samplers, respectively, installed thereon can be detached from the sample body holder and replaced. Once the first sample body holder has been removed, the agitating element is accessible and, since it is detachably installed on the drive shaft, it can also be removed from the container. Now the second sample body holder is also accessible, which means that the sample bodies or passive samplers, respectively, supported thereon can be exchanged. This construction thus permits easy replacement of the passive samplers or sample bodies, respectively. It is particularly preferable that the second sample body holder is also detachably held on the side wall, because then replacement of the sample bodies at the second sample body holder does not have to occur inside the container, but that this replacement may instead occur outside the container.

The outlet or the inlet can be connected to a flow measuring device, so that the flow rate through the container can be continuously detected. In addition, this makes it possible to determine the entire water volume that has flowed through the container during a measurement.

The container can optionally have a circular cross-section perpendicular to the longitudinal axis and the end faces extend perpendicular to the longitudinal axis. Such a circular-symmetrical construction has the advantage that, thanks to the rotating agitating element, there are then hardly any dead zones in the container and a continuous exchange of the fluid or of the water, respectively, takes place therein.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
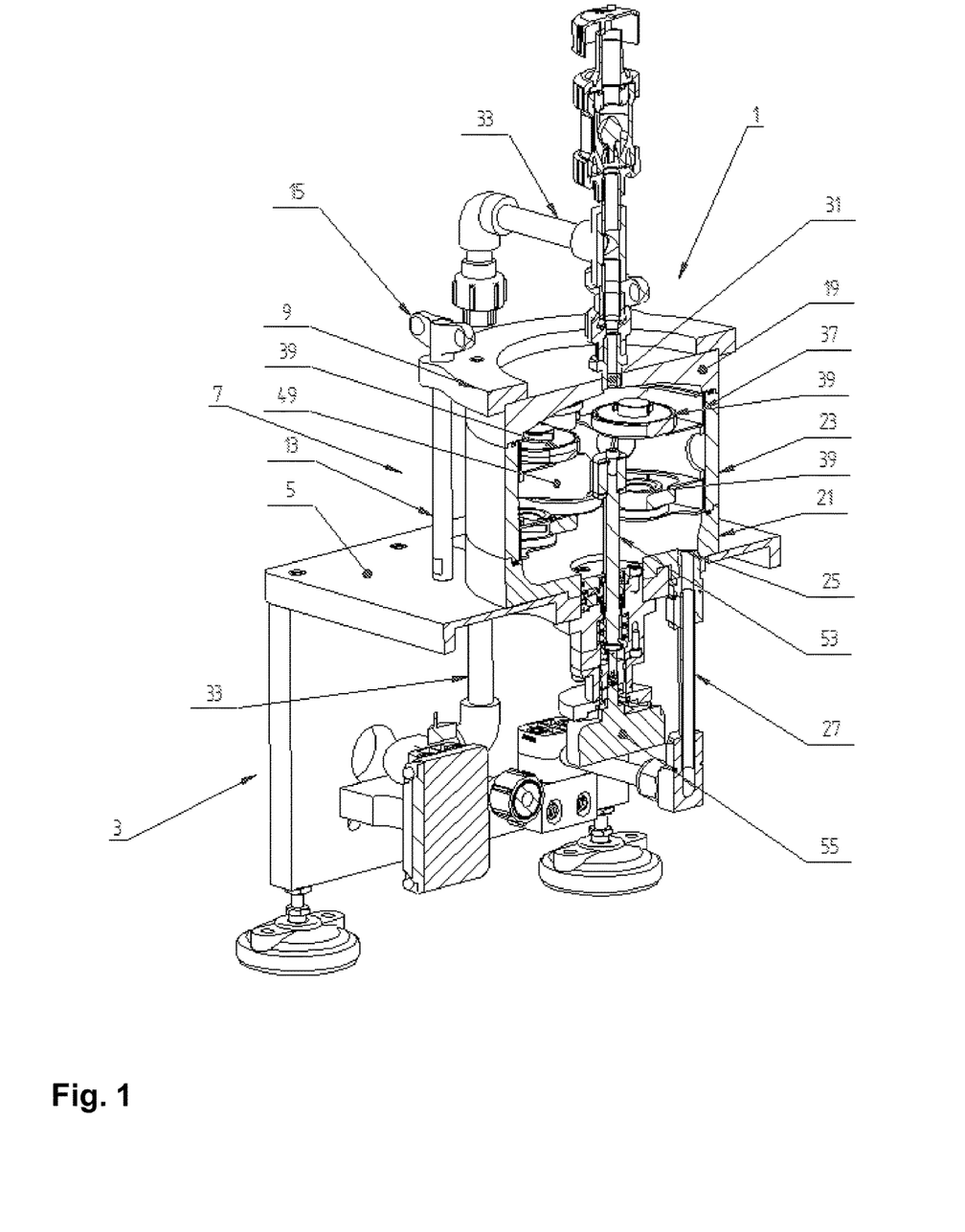
FIG. 1 is a perspective sectional view of a device for the exposure of sample bodies in a fluid, the device being constructed in accordance with the teachings of the present disclosure.
Figure 2:
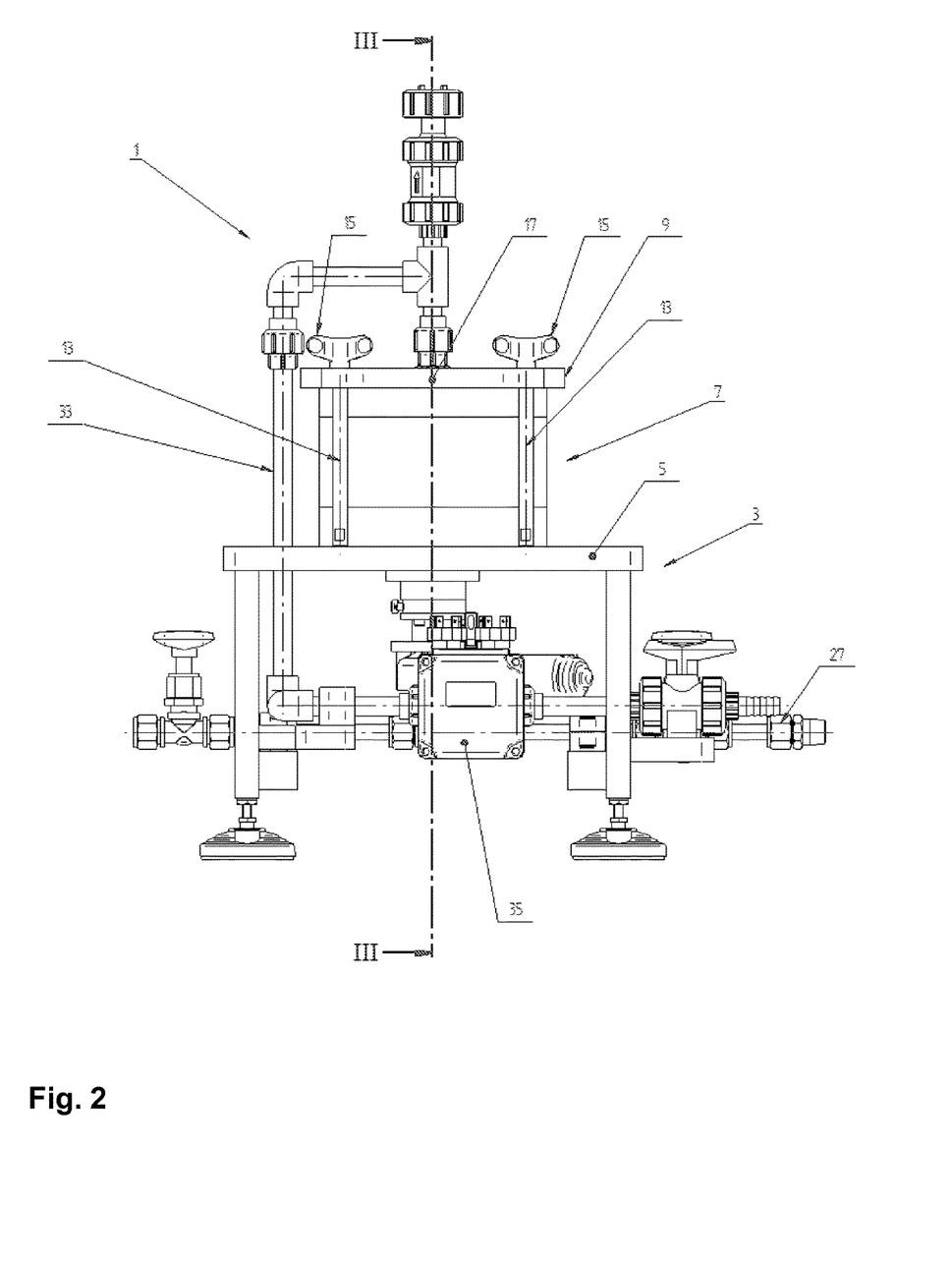
FIG. 2 is a side view of the device of FIG. 1.

With reference to FIG. 1, an exemplary device 1 constructed in accordance with the teachings of the present disclosure is illustrated. The device 1 is configured to expose sample bodies in a fluid, such as water. The device 1 can be supported on a bench 3, which comprises a counter 5 extending horizontally and which is preferably made of plastic.

The device 1 can comprise a closed container 7, which can be arranged between an upper clamping ring 9 and the bench counter 5. Extending between the clamping ring 9 and the bench counter 5 are threaded rods 13, so that the upper clamping ring 9 can be clamped against the bench counter 5 with the help of clamping nuts 15.

The container 7 can be designed such that it extends along a longitudinal axis 17 and has a circular cross-section perpendicular to the longitudinal axis 17. The container 7 can comprise a first upper end face 19 and a second bottom end face 21, between which a closed side wall 23 extending parallel to the longitudinal axis 17 is provided. The end faces 19, 21 and the side wall 23 in the preferred exemplary embodiment described here are made of polypropylene.

The first end face 19, the side wall 23 and the second end face 21 can be detachably connected to each other, wherein between the first end face 19 and the side wall 23 and also between the side wall 23 and the second end face 21 all-round seals can be arranged in each case. The end faces 19, 21 and the side wall 23 can be pressed against each other, for example by means of the clamping ring 9, which is clamped by means of the clamping nuts 15 against the bench counter 5, so that the container 7 is sealed in the region of the interfaces between the end faces 19, 21 and the side wall 23. Thus, the volume inside the container 7 can be isolated from the surrounding environment.

Figure 3:
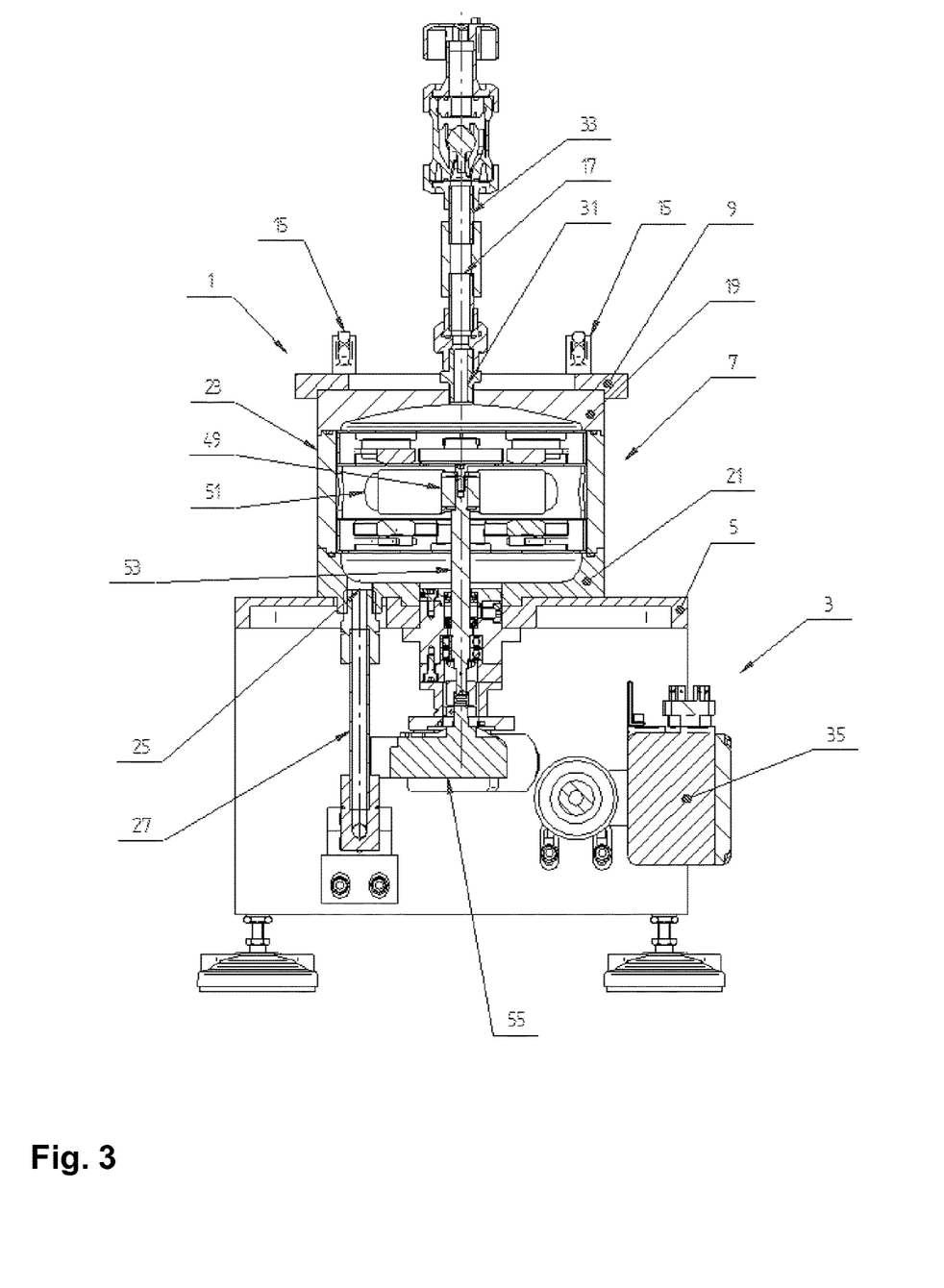
FIG. 3 is a sectional view taken along the line III-III of FIG. 2.
Figure 4:
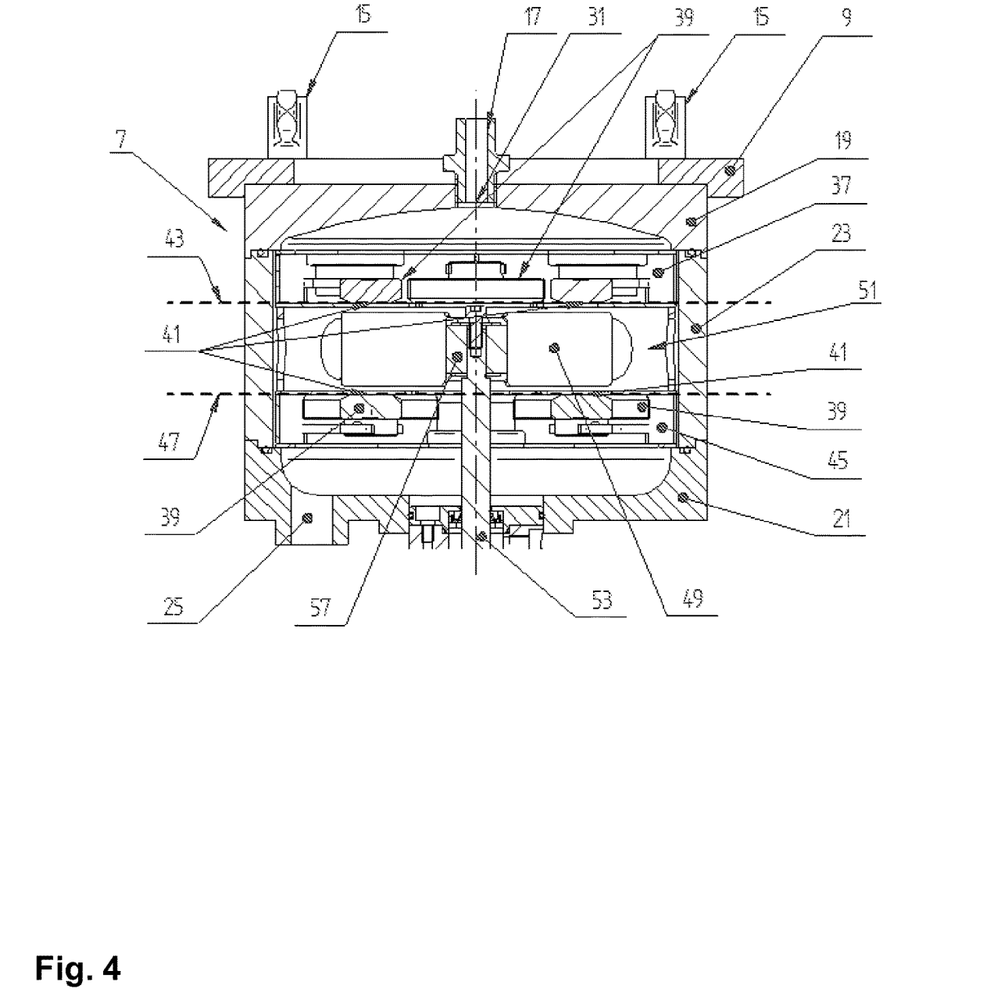
FIG. 4 is an enlarged portion of FIG. 3.

In FIGS. 1, 3 and 4, an inlet 25 is provided in the second bottom end face 21 radially offset relative to the longitudinal axis 17. Water can flow into the inside of the container 7 through the inlet 25. The inlet 25 can be connected via a pipe 27, which may be made of perfluoroalkoxy alkane (PFA), to a feed pump (not shown), which can ensure a constant volumetric flow rate. An outlet 31 can be provided in a central position in the upper first end face 19. The outlet 31 can be connected via a pipe 33, which can be made of polyvinylidene fluoride (PVDF), to a flow measuring device in the form of a flow sensor arrangement 35, by means of which the volumetric flow rate through the pipe 33 can be measured. In addition, by means of the flow sensor arrangement 35, the total volume of water that has flowed through the container 7 in a certain period of time can be determined.

A first sample body holder 37 can be arranged inside the container 7. The first sample body holder 37 can be provided next to the first end face 19 and can be detachably held on the side wall 23. The sample body holder 37 can be made of titanium (gr. 1; material no. 3.7025), and during the measurement operation it can accommodate sample bodies 39, which are designed such that certain substances contained in the water, such as pollutants, accumulate in them, wherein these substances can by means of an active surface section 40 diffuse into the inside of the sample body 39, which can have a collection phase having high affinity for the substances in question. Such so-called passive samplers are well known from the prior art, for example the Chemcatcher Metal sampler or the DGT sampler.

The active surface section 40 of the sample body 39 can define a measuring plane 41. When the active surface section 40 is designed as a flat membrane, the active surface section 40 and the measuring plane 41 can be coextensive. However, it is also conceivable that the active surface section 40 can have a curved shape. Then the measuring plane 41 is defined by a tangential plane, which contacts the center point of the active surface section 40.

Figure 5:
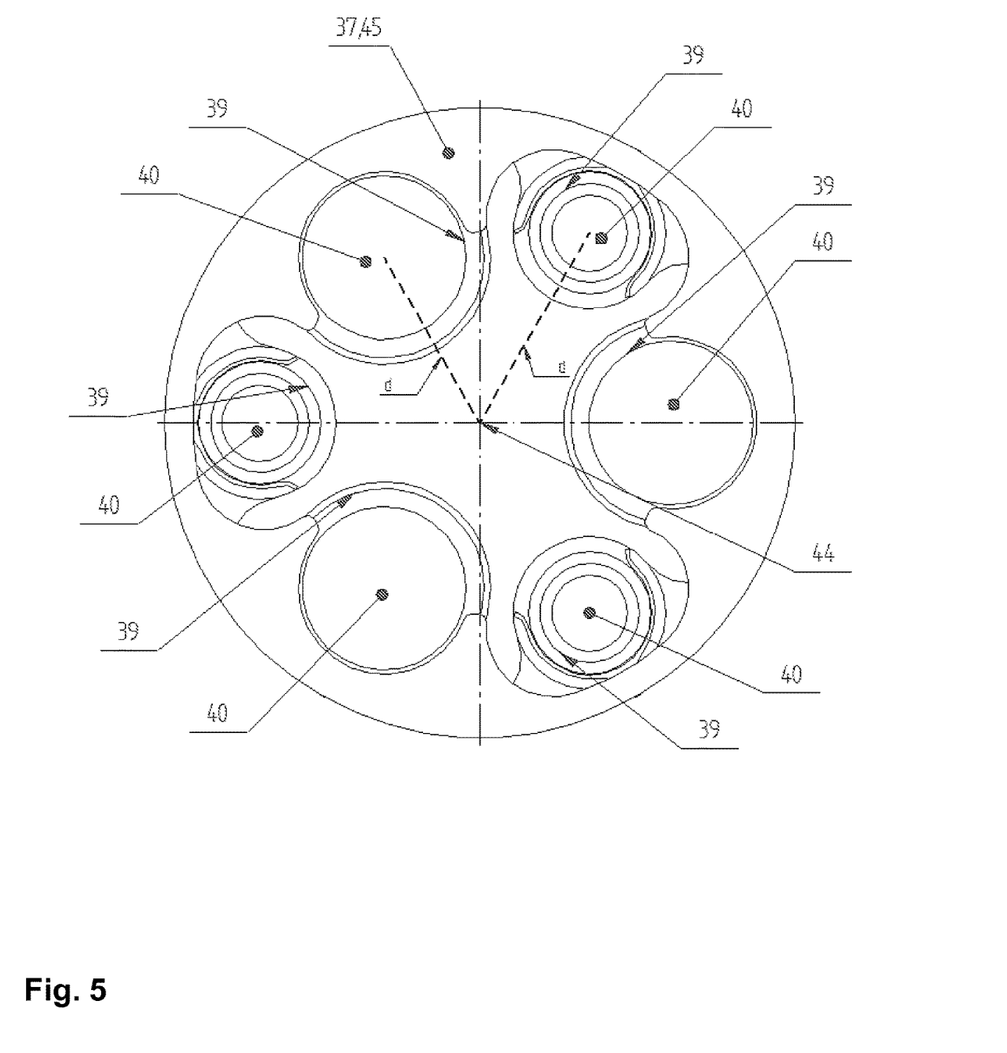
FIG. 5 is a top view of a portion of the device of FIG. 1, illustrating a sample body holder in more detail.

As can also be seen from FIG. 5, sample bodies 39 of different types can be installed in the first sample body holder 37, wherein the sample bodies 39 can be detachably attached in appropriate clamping devices in the sample body holder 37. The active surface sections 40 of the sample bodies 39 can face in a common direction, and the first sample body holder 37 can be designed such that it can support the sample bodies 39 in such a detachable manner that their measuring planes 41 extend in a common first sample plane 43 (see FIG. 4). In addition, the first sample body holder 37 can be designed such that the sample bodies 39 are supported therein in such a way that their center points have the same uniform distance "d" from the center point 44 of the first sample body holder 37. The sample bodies 39 can thus be arranged in a circle around the center point 44.

When the first sample body holder 37 is installed in the container 7, the active surface sections 40 can face away from the first end face 19, and the center point 44 of the first sample body holder 37 can coincide with the longitudinal axis 17. The active surface sections 40 can thus face away from the first end face 19 towards a center plane of the container 7, which can lie perpendicular to the longitudinal axis 17, and they can be arranged in a circle around the longitudinal axis 17. Thus, the center points of the sample bodies 39 can have a uniform distance to the longitudinal axis 17.

Optionally, a second sample body holder 45 can be provided in the container 7. The second sample body holder 45 can also be detachably held on the side wall 23 and which can be arranged adjacent to the second bottom end face 21. The second sample body holder 45 can likewise made of titanium (gr. 1; material no. 3.7025) and can be designed such that it can detachably support the afore-mentioned sample bodies 39 in such a way that their measuring planes 41 extend in a second sample plane 47 and the active surface sections 40 face away from the second end face 21 and towards the first end face 19 and, thus, towards the first sample plane 43. Thus, the sample bodies 39 can be arranged in the sample body holders 37, 45 in such a way that their active surface sections 40 are opposite each other. Incidentally, the second sample body holder 45 can be designed the same as the first, so that if desired, the sample bodies 39 can have an identical distance from the center point 44, and/or the center point 44 can coincide with the longitudinal axis 17 when the second sample body holder 45 is mounted in the container 7.

An agitating element 51 can be provided between the sample planes 43, 47. The agitating element 51 can extend radially outwards from the longitudinal axis 17 and can include blades 49. The agitating element can be formed of titanium (gr. 1; material no. 3.7025). The blades 49 can be detachably installed on a drive shaft 53 that can extend along the longitudinal axis 17. The drive shaft can extend through the second bottom end face 21 to a drive motor 55 and can be made of titanium (gr. 2; material no. 3.7035). A seal (not specifically shown), such as a PTFE shaft seal, can be disposed between the second bottom end face 21 and the drive shaft 53.

The blades 49 can be designed planar and can extend essentially parallel to the longitudinal axis 17. In addition, the blades 49 can be attached to a hub 57, which in turn can be screwed onto the drive shaft 53, so that by removing the hub 57 the agitating element 51 comprising the blades 49 can be removed from the drive shaft 53.

The previously described device can now be operated in the manner described below in order to expose the sample bodies 39 continuously in a fluid, e.g. in water from a body of water. The choice of the materials for the elements which come into contact with the water to be analyzed ensures that any risk of contamination from trace elements is removed as much as possible, and this makes an application in salt water possible.

To this purpose, the water can be pumped through the inlet 25 into the inside of the container 7 and can leave the container 7 through the outlet 31 and the pipe 33. This can provide a movement of the water through the container 7 essentially parallel to the longitudinal axis 17. By means of the flow sensor 35 the volumetric flow rate at which the water flows through the container 7 can be determined. It is also possible to measure the total volume of water that is pumped through the container in a certain period of time.

At the same time the agitating element 51 rotates with the blades 49, so that the water is continuously being moved over the active surface sections 40 of the sample bodies 39 or passive samplers, respectively. This ensures a continuous turbulence and circulation around the active surface sections 40 and it also prevents floating particles from being deposited on the active surface sections 40 or the build-up thereon of vegetation, both of which would impede the diffusion of the substances to be absorbed by the sample bodies 39 through the active surface sections 40. The constant rotation of the agitating element 51 by the drive motor 55 additionally causes flow conditions in the zone of the active surface sections 40 that remain constant over time, even over long periods. Thus, the conditions in which the sample bodies 39 are exposed to the water in question are reproducible and constant over time.

In situations where the sample bodies 39 or passive samplers, respectively, are arranged in the sample body holders 37, 45 in a circle around the center point 44, the flow rate at the active surface sections 40 is easily obtained from the rotation speed of the agitating element 51 and the distance "d" of the sample bodies 39 from the center point 44 because the arrangement in the container 7 renders this circle concentric to the longitudinal axis 17 around which the agitating element 51 rotates.

In the particular example provided, removal of the sample bodies 39 from the device 1 for analysis after the elapse of a predetermined measurement period can comprise: loosening the clamping nuts 15; removing the clamping ring 9; emptying the container 7; removing the first end face 19 and the first sample body holder 37 from the container 7; removing the hub 57 from the drive shaft 53 to remove the agitating element 51 from the container 7; optionally removing the second sample body holder 45 from the container 7; and removing the sample bodies 39 from the second sample body holder 45.

The side wall 23 and the first end face 21 can also be separated from each other if this is necessary for cleaning purposes.

Thus, the device 1 can also be easily disassembled, and the sample bodies 39 can be easily replaced.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for the continuous exposure of one or more sample bodies (39) in a fluid, each of the sample bodies comprising an active surface section (40) that defines a sampling plane (41), the device comprising:
    a container (7) that extends along a longitudinal axis (17), the container having a closed side wall (23), which extends along the longitudinal axis (17), and first and second end faces (19, 21) that extending transverse to the longitudinal axis, the container having an inlet and an outlet;
    a first sample body holder (37), which extends transverse to the longitudinal axis (17) and which is configured to support a first one of the one or more sample bodies (39) such that the sampling plane (41) of the first one of the one or more sample bodies (39) extends perpendicular to the longitudinal axis (17) in a first sample plane (43), and the active surface section (40) of the first one of the one or more sample bodies (39) faces away from the first end face (19); and
    an agitating element (51) that is coupled to the container for rotation in a plane perpendicular to the longitudinal axis (17), the agitating element being disposed on the side facing away from the first end face (19);
    wherein the agitating element (51) rotates about the longitudinal axis (17) and wherein the first sample body holder (37) is configured to hold a plurality of the sample bodies (39) such that their center points parallel to the first sample plane (43) have a uniform distance (d) to the longitudinal axis (17); and
    wherein the agitating element (51) is coupled to a drive shaft (53) that extends parallel to the longitudinal axis (17) through one of the first and second end faces (19, 21) and wherein the agitating element comprises blades (49) that extend radially outwards from the drive shaft (53).

2. The device of claim 1, further comprising a second sample body holder (45) that extends transverse to the longitudinal axis (17), the second sample body holder (45) being configured to support a second one of the one or more sample bodies (39) such that the sampling plane (41) of the second one of the one or more sample bodies (39) extends perpendicular to the longitudinal axis (17) in a second sample plane (47) and the active surface section (40) of the second one of the one or more sample bodies (39) faces away from the second end face (21), and wherein the agitating element (51) is arranged between the first and second sample body holders (37, 45).

3. The device of claim 2, wherein the second sample body holder (45) is detachably held on the side wall (23).

4. The device of claim 3, wherein the first end face (19) is detachably coupled to the side wall (23), wherein the drive shaft (53) extends through the second end face (21), and wherein the first sample body holder (45) is detachably held on the side wall (23).

5. The device of claim 2, wherein the second sample body holder (45) is configured to support a plurality of the one or more sample body holders (45) such that their center points parallel to the second sample plane (47) have a uniform distance (d) to the longitudinal axis (17).

6. The device of claim 5, wherein the inlet (25) is provided in one of the first and second end faces (19, 21) and wherein the outlet (31) is provided in the other one of the first and second end faces (19, 21).

7. The device of claim 1, wherein the blades (49) are detachably held on the drive shaft (53).

8. The device of claim 7, wherein the second sample body holder (45) is detachably held on the side wall (23).

9. The device of claim 1, wherein the first end face (19) is detachably coupled to the side wall (23), wherein the drive shaft (53) extends through the second end face (21), and wherein the first sample body holder (45) is detachably held on the side wall (23).

10. The device of claim 1, further comprising a flow measuring device (35) coupled in fluid communication with the container (7).

11. The device of claim 1, wherein the container (7) has a circular cross-section perpendicular to the longitudinal axis (17), and wherein the first and second end faces (19, 21) extend perpendicular to the longitudinal axis (17).

12. The device of claim 1, wherein the inlet (25) is provided in one of the first and second end faces (19, 21) and wherein the outlet (31) is provided in the other one of the first and second end faces (19, 21).

13. The device of claim 12, wherein the blades (49) are detachably held on the drive shaft (53).

14. The device of claim 13, further comprising a second sample body holder (45) that extends transverse to the longitudinal axis (17), the second sample body holder (45) being configured to support a second one of the one or more sample bodies (39) such that the sampling plane (41) of the second one of the one or more sample bodies (39) extends perpendicular to the longitudinal axis (17) in a second sample plane (47) and the active surface section (40) of the second one of the one or more sample bodies (39) faces away from the second end face (21), and wherein the agitating element (51) is arranged between the first and second sample body holders (37, 45), and wherein the second sample body holder (45) is detachably held on the side wall (23).

15. The device of claim 12, wherein the first end face (19) is detachably coupled to the side wall (23), wherein the drive shaft (53) extends through the second end face (21), and wherein the first sample body holder (45) is detachably held on the side wall (23).

* * * * *